(12) United States Patent
Lisogurski et al.

(10) Patent No.: US 8,712,492 B2
(45) Date of Patent: Apr. 29, 2014

(54) PHOTON DENSITY WAVE BASED DETERMINATION OF PHYSIOLOGICAL BLOOD PARAMETERS

(75) Inventors: Daniel Lisogurski, Boulder, CO (US); Doug P. Miller, Lakewood, CO (US); Friso Schlottau, Lyons, CO (US); Youzhi Li, Longmont, CO (US); Andy S. Lin, Boulder, CO (US); Edward M. McKenna, Boulder, CO (US)

(73) Assignee: Covidien LP, Mansfield, MA (US)

( * ) Notice: Subject to any disclaimer, the term of this patent is extended or adjusted under 35 U.S.C. 154(b) by 295 days.

(21) Appl. No.: 13/149,606

(22) Filed: May 31, 2011

(65) Prior Publication Data

US 2012/0310058 A1    Dec. 6, 2012

(51) Int. Cl.
*A61B 5/1455*    (2006.01)

(52) U.S. Cl.
USPC .......................... 600/322; 600/310; 600/324

(58) Field of Classification Search
USPC ................................................. 600/309–344
See application file for complete search history.

(56) References Cited

U.S. PATENT DOCUMENTS

| | | |
|---|---|---|
| 5,413,100 A | 5/1995 | Barthelemy et al. |
| 5,555,855 A | 9/1996 | Takahashi |
| 6,058,324 A | 5/2000 | Chance |
| 6,192,260 B1 | 2/2001 | Chance |
| 6,246,892 B1 | 6/2001 | Chance |
| 2008/0139908 A1 | 6/2008 | Kurth |
| 2010/0081899 A1* | 4/2010 | McKenna ............ 600/324 |
| 2011/0071373 A1 | 3/2011 | Li et al. |

FOREIGN PATENT DOCUMENTS

| | | |
|---|---|---|
| RU | 2038037 | 6/1995 |
| RU | 2040912 | 8/1995 |

OTHER PUBLICATIONS

Vasilis Ntziachristos, et al.; "Oximetry Based on Diffuse Photon Density Wave Differentials;" Medical Physics; Feb. 2000; pp. 410-421; vol. 27, No. 2; Am. Assoc. Phys. Med.; Melville, NY, US.

* cited by examiner

*Primary Examiner* — Eric Winakur
*Assistant Examiner* — Marjan Fardanesh

(57) ABSTRACT

A system for measuring a physiological parameter of blood in a patient is presented. The system includes a transmission module configured to emit a plurality of photon density waves into tissue of the patient from a plurality of modulated light sources. The system also includes a receiver module configured to detect characteristics of the plurality of photon density waves. The system also includes a processing module configured to identify characteristics of a pulsatile perturbation of the tissue based on the characteristics of the plurality of photon density waves, and identify a value of the physiological parameter based on at least the characteristics of the pulsatile perturbation of the tissue and the characteristics of the plurality of photon density waves.

20 Claims, 9 Drawing Sheets

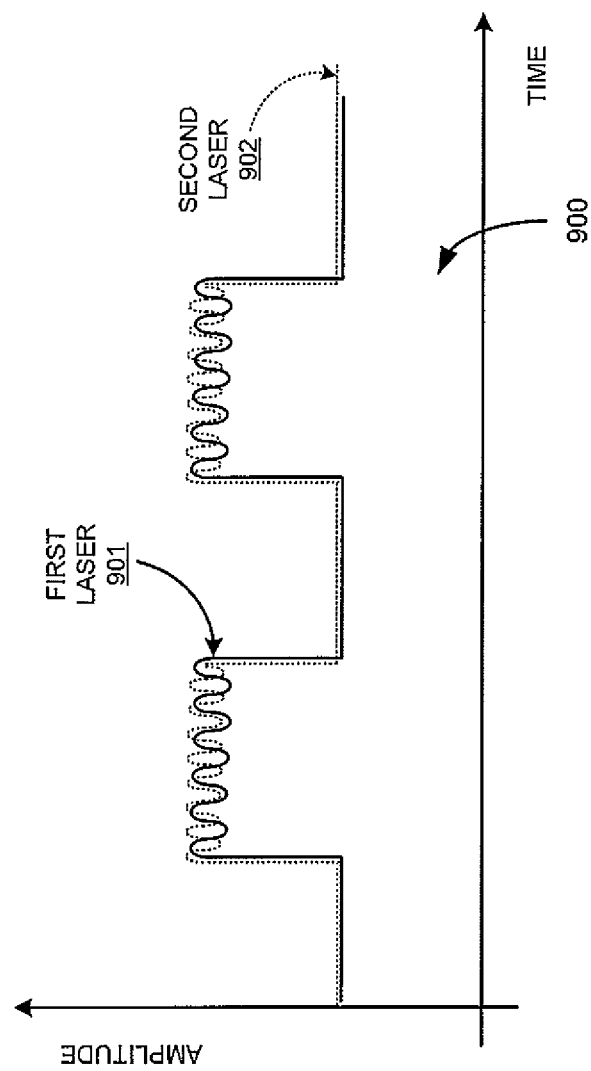

US 8,712,492 B2

PHOTON DENSITY WAVE BASED DETERMINATION OF PHYSIOLOGICAL BLOOD PARAMETERS

TECHNICAL FIELD

Aspects of the disclosure are related to the field of medical devices, and in particular, measuring physiological parameters of blood based on photon density waves emitted into tissue.

TECHNICAL BACKGROUND

Various devices, such as pulse oximetry devices, can measure some parameters of blood flow in a patient, such as heart rate and oxygen saturation of hemoglobin. Pulse oximetry devices are a non-invasive measurement device, typically employing solid-state lighting elements, such as light-emitting diodes (LEDs) or solid state lasers, to introduce light into the tissue of a patent. The light is then detected and analyzed to determine the parameters of the blood flow in the patient. However, conventional pulse oximetry devices typically only measure certain blood parameters, and are subject to patient-specific noise and inconsistencies which limits the accuracy of such devices.

Overview

A system for measuring a physiological parameter of blood in a patient is presented. The system includes a transmission module configured to emit a plurality of photon density waves into tissue of the patient from a plurality of modulated light sources. The system also includes a receiver module configured to detect characteristics of the plurality of photon density waves. The system also includes a processing module configured to identify characteristics of a pulsatile perturbation of the tissue based on the characteristics of the plurality of photon density waves, and identify a value of the physiological parameter based on at least the characteristics of the pulsatile perturbation of the tissue and the characteristics of the plurality of photon density waves.

A method of operating a system for measuring a physiological parameter of blood in a patient is also presented. The method includes emitting a plurality of photon density waves into tissue of the patient from a plurality of modulated light sources, and detecting characteristics of the plurality of photon density waves. The method also includes identifying characteristics of a pulsatile perturbation of the tissue based on the characteristics of the plurality of photon density waves, and identifying a value of the physiological parameter based on at least the characteristics of the pulsatile perturbation of the tissue and the characteristics of the plurality of photon density waves.

Another example system for measuring a physiological parameter of blood in a patient is also presented. The system includes a transmission module configured to emit a first modulated optical signal and a second modulated optical signal into tissue of the patient. The system also includes a receiver module configured to detect the first modulated optical signal and the second modulated optical signal propagated through the tissue during a pulsatile perturbation. The system also includes a processing module configured to process the detected first modulated optical signal and the detected second modulated optical signal to determine at least an amplitude and a phase delay of both the detected first modulated optical signal and the detected second modulated optical signal. The processing module is also configured to determine characteristics of the pulsatile perturbation of the tissue based on at least the amplitude and the phase delay of both the detected first modulated optical signal and the detected second modulated optical signal. The processing module is also configured to determine a value of the physiological parameter based on at least the characteristics of the pulsatile perturbation of the tissue and the amplitude and the phase delay of both the detected first modulated optical signal and the detected second modulated optical signal.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views. While several embodiments are described in connection with these drawings, the disclosure is not limited to the embodiments disclosed herein. On the contrary, the intent is to cover all alternatives, modifications, and equivalents.

FIG. 9 includes a graph illustrating example laser modulations.

DETAILED DESCRIPTION

Figure 1:
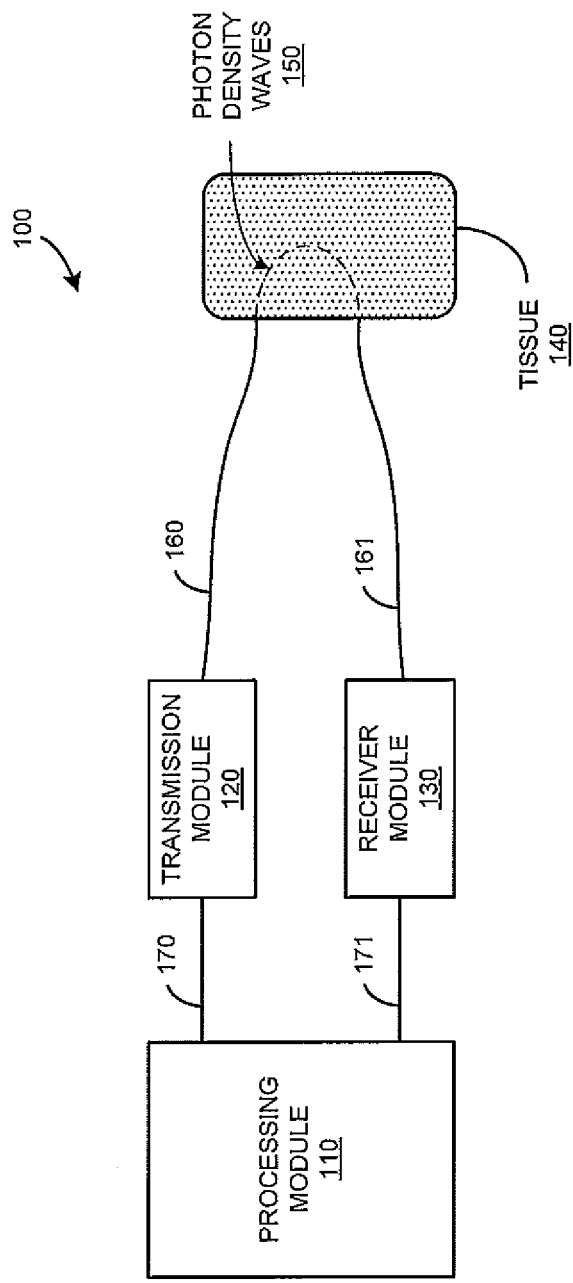
FIG. 1 is a system diagram illustrating a system for measuring a physiological parameter of blood in a patient.

FIG. 1 is a system diagram illustrating system 100 for measuring a physiological parameter of blood in a patient. FIG. 1 includes processing module 110, transmission module 120, receiver module 130, and tissue 140. Processing module 110 and transmission module 120 communicate over link 170. Processing module 110 and receiver module 130 communicate over link 171. Transmission module 120 emits optical signals over link 160. Receiver module 130 receives optical signals over link 161. In FIG. 1, link 160 and link 161 are shown located an exemplary distance apart, but could be located on the surface of tissue 140 at predetermined locations or distances. Tissue 140 is a portion of the tissue of a patent undergoing measurement of a physiological blood parameter, and is represented by a rectangular element for simplicity in FIG. 1. Although the term 'optical' is used herein for convenience, it should be understood that the measurement signals are not limited to visible light, and could comprise any photonic, electromagnetic, or energy signals, such as visible, infrared, ultraviolet, radio, or other signals.

Figure 2:
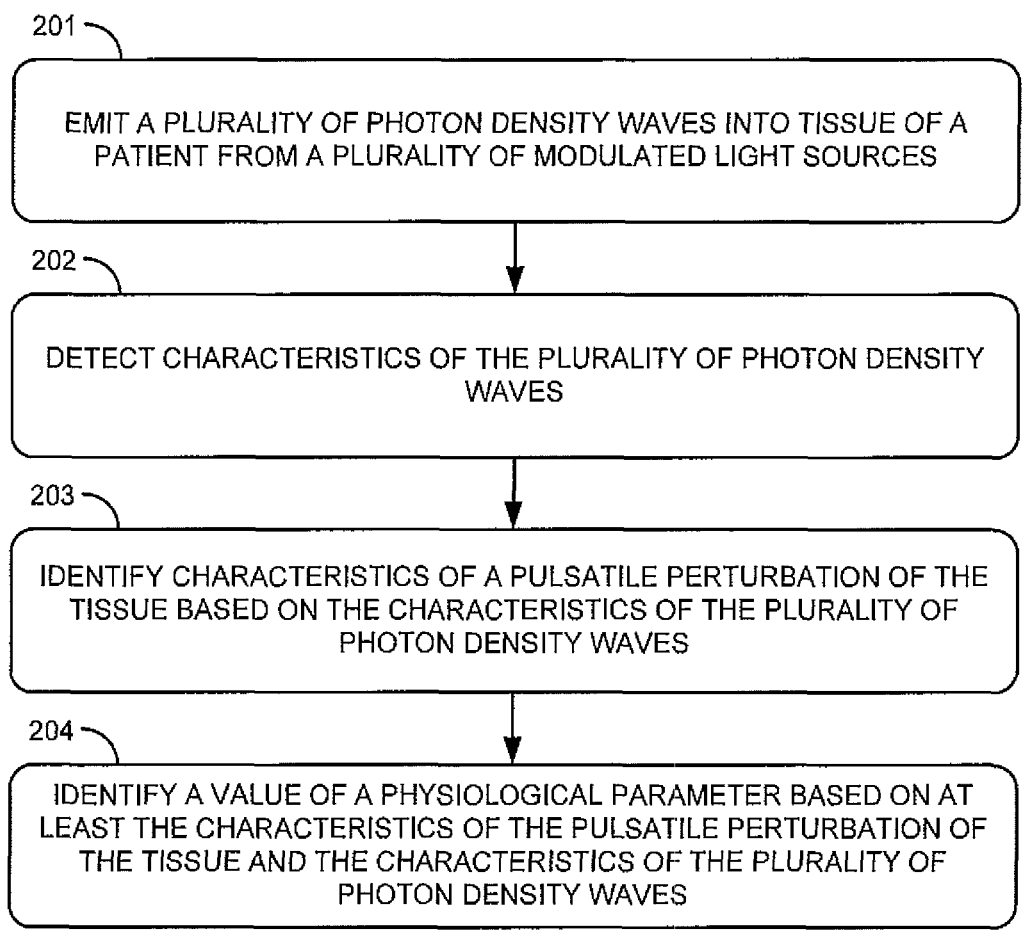
FIG. 2 is a flow diagram illustrating a method of operation of a system for measuring a physiological parameter of blood in a patient.

FIG. 2 is a flow diagram illustrating a method of operating system 100 for measuring a physiological parameter of blood in a patient. The operations of FIG. 2 are referenced herein parenthetically. In FIG. 2, transmission module 120 emits (201) a plurality of photon density waves into tissue 140 of a patient from a plurality of modulated light sources. In this example, transmission module 120 emits the plurality of photon density waves over link 160 into tissue 140. Link 160 could comprise an optical fiber or fibers, or other optical signal transmission apparatus. The plurality of photon density waves emitted into tissue 140 each comprise modulated optical signals, such as modulated laser light. In some examples, each of the plurality of photon density waves comprises at least an individual wavelength of modulated light. Transmission module 120 could receive instructions from processing module 110 regarding the plurality of photon density waves over link 170, among other instructions.

Receiver module 130 detects (202) characteristics of the plurality of photon density waves. In this example, receiver module 130 can detect the plurality of photon density waves over link 161 which were emitted into tissue 140 by transmission module 120. Link 161 could comprise an optical fiber or fibers, or other optical signal transmission apparatus. Receiver module 130 detects the plurality of photon density waves in tissue 140 as modulated optical signals. Receiver module 130 typically detects the characteristics of the plurality of photon density waves after being scattered, absorbed, propagated, or transmitted by tissue 140. The characteristics could include amplitude, phase delay, noise, modulations, or other characteristics of each of the plurality of photon density waves. Receiver module 130 then transfers information about the characteristics of the plurality of photon density waves over link 171.

Processing module 110 identifies (203) characteristics of a pulsatile perturbation of tissue 140 based on the characteristics of the plurality of photon density waves. Processing module receives information about the characteristics of the plurality of photon density waves over link 171. In this example, the pulsatile perturbation comprises a change in arterial blood volume due to the ejection of blood from the heart. In other examples, the pulsatile perturbation comprises a vascular palpitation induced by the heart of the patient, although other pulsatile perturbations could be employed including venous volume changes induced by respiration.

Characteristics of the pulsatile perturbation include time-based characteristics of the pulsatile perturbation, such as volumetric changes over time of tissue 140. For example, the characteristics of the received photon density waves may be time varying, such as when the heart of the patient ejects blood and the number of absorbing and scattering particles between the emitted photon density waves and detected photon density waves is greater at some points in the cardiac cycle than others. It should be understood that a time delay between the cardiac cycle and the measurement at a location such as the finger may exist, and the time delay may be time-varying, such as during a respiratory cycle. The characteristics of the pulsatile perturbation could be represented by a pulsatile waveform of the characteristics of the plurality of photon density waves, such as a photoplethysmograph (PPG) including amplitudes or phase delays of the plurality of photon density waves over a predetermined timeframe, although other representations could be employed.

Processing module 110 identifies (204) a value of a physiological parameter based on at least the characteristics of the pulsatile perturbation of tissue 140 and the characteristics of the plurality of photon density waves. The physiological parameter could include any parameter associated with blood or tissue 140 of the patient, such as total hemoglobin concentration (tHb), regional oxygen saturation (rSO2), or arterial oxygen saturation (SpO2), among other parameters, including combinations thereof. The characteristics of the plurality of photon density waves can change during pulsatile perturbation of tissue 140. These changing photon density wave characteristics are processed along with the pulsatile perturbation characteristics to determine a value of the physiological parameter.

In typical examples, the pulsatile perturbation introduces dynamic, quasi-periodic, or "AC" information into the characteristics of the plurality of photon density waves, and the dynamic characteristics could be processed to determine a value of the physiological parameter. For example, the pulsatile perturbation characteristics could provide an AC amplitude and AC phase delay for each of the plurality of photon density waves, which are then processed to determine a value of the physiological parameter. Time-averaged characteristics, such as "DC" information, could also be taken into account. In some examples, the AC amplitude and AC phase delay could be determined by determining multiple measurements of the amplitude and phase delay over the pulsatile perturbation, and determining differential values of each of the amplitude and phase delay based on the multiple measurements. A ratio of the differential values could then be processed to determine the value of the physiological parameter. The multiple measurements could be taken at similar points during a periodic pulsatile perturbation, such as during subsequent minimal perfusion or blood flow rate times. The multiple measurements could be taken continuously during the pulsatile perturbation, or at varying points during a periodic pulsatile perturbation, such as at maximum perfusion and minimum perfusion times. It should be understood that the terms "AC" and "DC" used herein are not necessarily referring to alternating or direct "currents," but are instead used to refer to dynamic signal properties for "AC" and relatively stable signal properties for "DC."

Figure 3:
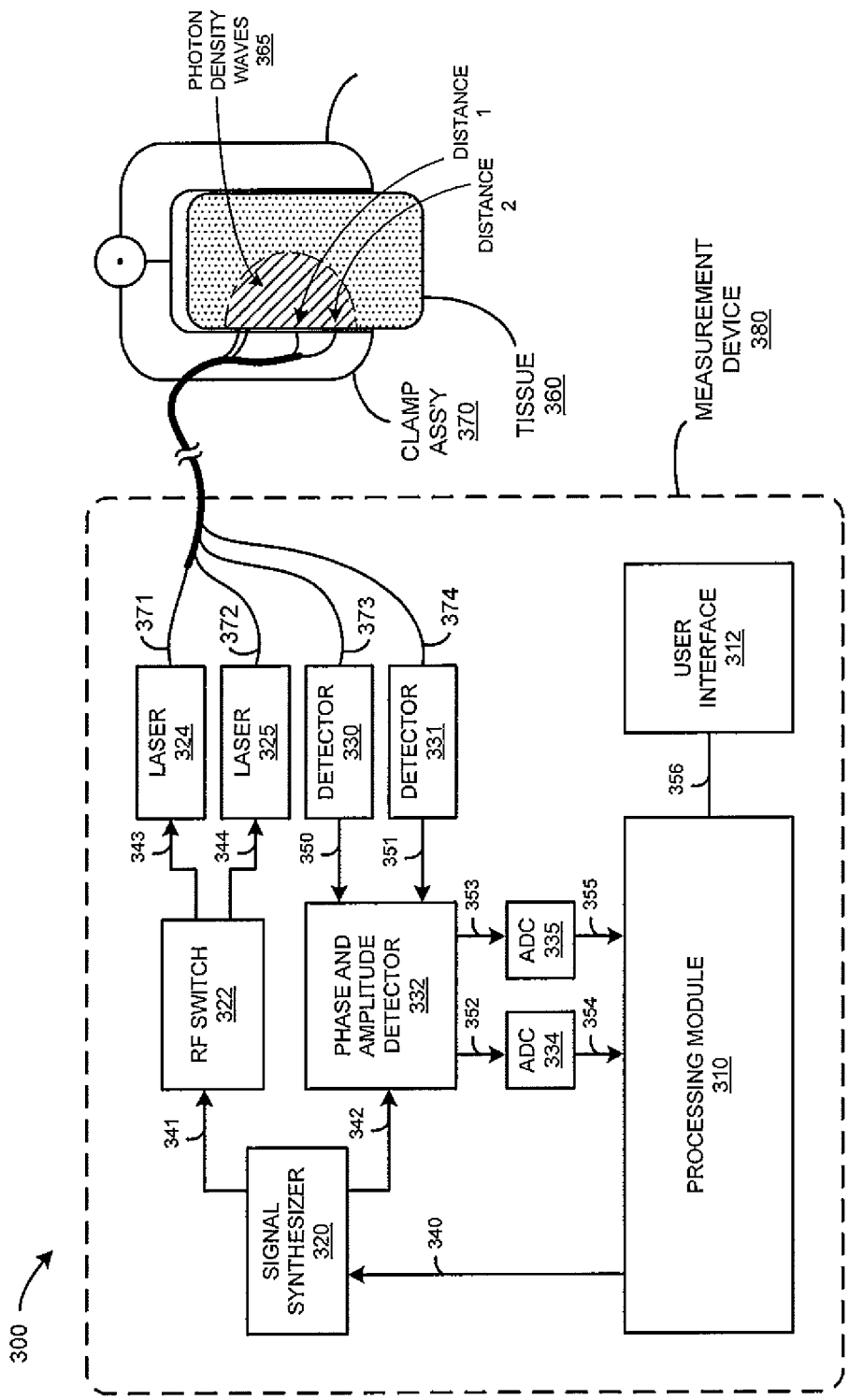
FIG. 3 is a system diagram illustrating a system for measuring a physiological parameter of blood in a patient.

FIG. 3 is a system diagram illustrating system 300 for measuring a physiological parameter of blood in a patient. System 300 includes tissue 360, clamp assembly 370, and measurement device 380. Measurement device 380, in conjunction with clamp assembly 370 is one example embodiment of a system for measuring a physiological parameter of blood in tissue 360 of a patient. Tissue 360 is a portion of the tissue of a patent undergoing measurement of a physiological blood parameter, and is represented by a rectangular element for simplicity in FIG. 3. It should be understood that tissue 360 could represent a finger, fingertip, toe, earlobe, forehead, or other tissue portion of a patient undergoing physiological parameter measurement. Tissue 360 could comprise muscle, fat, blood, vessels, or other tissue components. The blood portion of tissue 360 could include tissue diffused blood and arterial or venous blood.

Clamp assembly 370 includes a clamp portion and an optical signaling portion. The clamp portion is configured to compressively clamp over a portion of tissue 360 to provide optical mating between ends of optical fibers 371-374 and tissue 360, and could comprise metal, plastic, or composite materials to form the clamp jaw portion. A spring hinge or other element could provide the compressive force to hold clamp assembly 370 onto tissue 360. Other configurations could be employed to provide optical contact between ends of optical fibers 371-374 and tissue 360, such as adhesive pads. Clamp assembly 370 also includes an optical signaling portion which includes optical fibers 371-374. A sheath or loom could be employed to bundle each of optical fibers 371-374 together for convenience. One end of each of optical fibers 371-374 mates with an associated component of measurement device 380, and the other end of each of optical fibers 371-374 is configured to emit light into tissue 360 or receive light from tissue 360. Optical fibers 371-374 each comprise an optical waveguide, such as a glass or polymer fiber, for transmission of light therein, and could include multimode fiber (MMF) or single mode fiber (SMF) materials.

In FIG. 3, optical fibers 371-374 are bundled into a group at measurement device 380, and broken apart into separate fibers at clamp assembly 370. The order/numbering of the optical fiber breakout is the same as that shown for the bundling, i.e. 371 is on 'top' and 374 is on 'bottom' of FIG. 3. Also shown in FIG. 3 are different distances or spacings for each of the receiving optical fibers 373-374, as compared to the emission fibers 371-372. The distances are indicated by 'distance 1' and 'distance 2' in FIG. 3. These distances could be determined based on the parameters or characteristics of the tissue or blood are to be monitored, or upon the differences in signal detection at the two distances. For example, 'distance 1' could be 7 millimeters, and 'distance 2' could be 10 millimeters, although other distances could be used. In FIG. 3, the emission fibers 371-372 as shown to be closely spaced, and could be considered to be at the same contact point on tissue 360, possibly aligned along a spatial dimension protruding from FIG. 3. Also, the configuration of clamp assembly 370 shown in FIG. 3 is for a reflectance-based measurement, where emit and receive fibers are coupled to the same side of tissue 360. In other examples, a transmission-based measurement could be employed, where emit and receive fibers are on opposite sides of tissue 360. A combination of reflectance and transmission could be employed.

Measurement device 380 includes processing module 310, user interface 312, signal synthesizer 320, radio frequency (RF) switch 322, lasers 324-325, detectors 330-331, phase and amplitude (PA) detector 332, and analog to digital converters (ADC) 334-335. Processing module 310 and signal synthesizer 320 communicate over link 340. Processing module 310 and ADC 334-335 communicate over associated links 354-355. Processing module 310 and user interface 312 communicate over link 356. Signal synthesizer 320 and RF switch 322 communicate over link 341. Signal synthesizer 320 and PA detector 332 communicate over link 342, RF switch 322 and lasers 324-325 communicate over associated links 343-344. PA detector 332 and ADC 334-335 communicate over associated links 352-353. PA detector 332 and detectors 330-331 communicate over associated links 350-351.

In FIG. 3, links 340-344 and 350-356 each use metal, glass, optical, air, space, or some other material as the transport media, and comprise analog, digital, RF, optical, or power signals, including combinations thereof. Links 340-344 and 350-356 could each use various communication protocols or formats, such as Controller Area Network (CAN) bus, Inter-Integrated Circuit (I2C), 1-Wire, Radio Frequency Identification (RFID), optical, circuit-switched, Internet Protocol (IP), Ethernet, Wireless Fidelity (WiFi), Bluetooth, communication signaling, or some other communication format, including combinations, improvements, or variations thereof. Links 340-344 and 350-356 could each be direct links or may include intermediate networks, systems, or devices, and could each include a logical link transported over multiple physical links.

Although various elements of system 300 are shown in FIG. 3 as included in measurement device 380, as indicated by the dashed box surrounding elements 310, 312, 320, 322, 324-325, 330-331, 332, 334-334, and the associated links, it should be understood other configurations could be employed. Also, the directional arrows shown for the interconnecting links in measurement device 380 are merely used to show an example operational flow, and are not intended to represent one-way communications.

Processing module 310 retrieves and executes software or other instructions to direct the operations of signal synthesizer 320 as well as process data received from ADC 334-335. In this example, processing module 310 comprises a digital signal processor (DSP), and could include a non-transitory computer-readable medium such as a disk, integrated circuit, server, flash memory, or some other memory device, and also may be distributed among multiple memory devices. Examples of processing system 310 include DSPs, microcontrollers, field programmable gate arrays (FPGA), or discrete logic, including combinations thereof. In one example, the DSP comprises an Analog Devices Blackfin® device.

User interface 312 includes equipment and circuitry to communicate information to a user of measurement device 380. User interface 312 may include any combination of displays and user-accessible controls and may be part of system 300 as shown or could be a separate patient monitor or multi-parameter monitor. When user interface 312 is a separate unit, user interface 312 may include a processing system and communication link 356 may be any suitable link for external communication such as a serial port, UART, USB, Ethernet, or wireless link such as Bluetooth, Zigbee or WiFI, among other link types. Examples of the equipment to communicate information to the user could include displays, indicator lights, lamps, light-emitting diodes, haptic feedback devices, audible signal transducers, speakers, buzzers, alarms, vibration devices, or other indicator equipment, including combinations thereof. The information could include raw ADC samples, calculated phase and amplitude information for one or more emitter/detector pairs, blood parameter information, waveforms, summarized blood parameter information, graphs, charts, processing status, or other information. User interface 312 also includes equipment and circuitry for receiving user input and control, such as for beginning, halting, or changing a measurement process or a calibration process. Examples of the equipment and circuitry for receiving user input and control include push buttons, touch screens, selection knobs, dials, switches, actuators, keys, keyboards, pointer devices, microphones, transducers, potentiometers, non-contact sensing circuitry, or other human-interface equipment.

Signal synthesizer 320 generates modulation signals and reference signals for use by other elements of measurement device 380, as well as receives instructions from processing module 310 for generating these signals. In this example, signal synthesizer 320 comprises a two-channel direct digital synthesis (DDS) component, such as Analog Devices AD9958. Signal synthesizer 320 digitally synthesizes drive signal 341 and reference signal 342 at a matched predetermined frequency and waveform, such as a 400 MHz sine wave, although other waveforms and frequencies could be employed. In some examples, a filtered output signal can be used or higher-frequency images of the output frequency can be isolated by filters and used to generate drive signal 341 or reference signal 342. Drive signal 341 and reference signal 342 are precisely synthesized with predetermined amplitude and phase delay relationships to each other. The amplitude of drive signal 341 is synthesized based on the input parameters for lasers 324-325, possibly after further amplification, switching, or multiplexing by RF switch 322. The amplitude of reference signal 342 is synthesized based on the input parameters of PA detector 332, although in some examples levels may be adjusted for optimal power consumption, dynamic range, signal to noise ratio at the receiver, or the operating characteristics of PA detector 332. The relative phase between drive signal 341 and reference signal 342 are synthesized based on the phase delay experienced by drive signal 341 through lasers 324-325, optical fibers 371-372, tissue 360, optical fibers 373-374, and detector 330-331, among other factors, such as operating parameters of PA detector 332. For example, the phase delay synthesized by signal synthesizer 320 may be calibrated to achieve a predetermined relative phase delay at PA detector 332, based in part on the length of optical fibers 371-374. Other examples of signal synthesizer 320 include multiple DDS components, CD/DVD laser driver components, such as National Semiconductor LMH6525, function generators, or other signal generation components. However, in examples of CD/DVD laser driver components, additional circuitry may be needed to achieve the precise predetermined amplitude and phase delay relationship between drive signal 341 and reference signal 342, such as filters, delay elements, or other calibration components.

RF switch 322 comprises switching, multiplexing, or buffering circuitry for selectively providing drive signal 341 over any of links 343-344. In this example, RF switch 322 comprises a single-pole double-throw (SPDT) style of switch operable at the high frequencies of drive signal 341 to alternately provide drive signal 341 to either of links 343-344 in a repeating, sequential manner. RF switch 322 could comprise a solid-state switch, such as transistors, RF junctions, diodes, or other solid state devices. In some examples, RF switch 322 receives switching instructions from processing module 310, while in other examples, a predetermined switching profile is included in RF switch 322. In further examples, RF switch 322 includes signal conditioning components, such as passive signal conditioning devices, attenuators, filters, and directional couplers, active signal conditioning devices, amplifiers, or frequency converters, including combinations thereof. In yet further examples, RF switch 322 provides drive signal 341 to both of links 343-344 in a simultaneous manner. In all configurations of RF switch 322, an "off" condition could be employed where drive signal 341 is not provided over any of links 343-344, and links 343-344 could be driven to a predetermined signal state, such as a zero signal level, predetermined DC signal level, or floating-state, among other configurations.

Lasers 324-325 each comprise a laser element such as a laser diode, solid-state laser, or other laser device, along with associated driving circuitry. Lasers 324-325 emit coherent light over associated optical fibers 371-372. In this example, a single wavelength of light is associated with each of lasers 324-325 and likewise each of optical fibers 371-372, and the wavelengths may be of different wavelengths, such as 660 nm for laser 324 and 808 nm for laser 325, although other wavelengths could be used. Each of lasers 324-325 modulate the associated laser light based on an input modulation signal, namely the associated modulation signal received over links 343-344. Optical couplers, cabling, or attachments could be included to optically mate lasers 324-325 to optical fibers 371-372. Additionally, a bias signal may be added or mixed into the modulation signals received over links 343-344, such as adding a "DC" bias for the laser light generation components. In some examples, the bias is adjusted so that the minimum signal level provided to the laser components is at the lasing threshold, or slightly above the lasing threshold. Further examples of the modulation can be seen in FIGS. 8 and 9.

Detectors 330-331 each comprise a light detector element, such as a photodiode, phototransistor, avalanche photodiode (APD), photomultiplier tube, charge coupled device (CCD), or other optoelectronic sensor, along with associated receiver circuitry such as amplifiers or filters. Detectors 330-331 receive light over associated optical fibers 373-374, and transfer electrical signals over links 350-351. Optical couplers, cabling, or attachments could be included to optically mate detectors 330-331 to optical fibers 373-374. Detectors 330-331 convert the optical signals received over optical fibers 373-374 to electrical signals for transfer over links 350-351. Detectors 330-331 could also include circuitry to condition or filter the signals before transfer over links 350-351. It should be noted that in this example output optical fibers 371-372 each only carry a particular wavelength of light, while input optical fibers 373-374 can carry any received light from tissue 360, which could include multiple wavelengths on each of optical fibers 373-374. Also, although two detectors are shown in FIG. 3, in other examples, a single detector could be shared between multiple laser sources, such as when the detector employs TDM, FDM, CDM, or WDM techniques to detect multiple PDW signals from a combined detected light.

Phase and amplitude (PA) detector 332 comprises circuitry and processing elements to determine amplitudes of signals received over links 350-351, and to determine phase delays of signals received over links 350-351 relative to reference signal 342. In some examples, PA detector 332 comprises a device, such as Analog Devices AD8302, although discrete circuitry could be employed. PA detector 332 provides the amplitude and phase information in an analog format over links 352-353. The phase and amplitude outputs of PA detector 332 could be amplified or conditioned to satisfy the input parameters of ADC 334-335.

ADC 334-335 each comprise analog to digital converters. ADC 334-335 receive the amplitude and phase information over associated links 352-353 from PA detector 332, and digitize the amplitude and phase information. The dynamic range, bit depth, and sampling rate of ADC 334-335 could be selected based on the signal parameters of the amplitude and phase information, such as to prevent aliasing, clipping, and for reduction in digitization noise. ADC 334-335 could each be a dual-channel ADC, or be implemented in discrete components. ADC 334-335 provides digitized forms of the amplitude and phase information over links 354-355 for receipt by processing system 310.

Although lasers 324-325 and detectors 330-331 are included in measurement device 380 in FIG. 3, in other examples, lasers 324-325 or detectors 330-331 could be included in clamp assembly 370. Shorter optical fibers 371-374 or other waveguides could be employed when lasers 324-325 or detectors 330-331 are integrated into clamp assembly 370. In some examples, optical fibers 371-374 are not employed between lasers 324-325 and tissue 360, and the laser light is introduced directly into tissue 360, possibly after associated lenses or tissue interface optics. Furthermore, electrical or RF signaling could be employed between clamp assembly 370 and measurement device 380 to drive or receive signals from lasers 324-325 or detectors 330-331.

Although two lasers are shown in FIG. 3 to drive two optical fibers, in other examples, a single optical fiber is employed and a single laser is employed. Also, a greater number of laser sources and detectors could be employed, such as four lasers or four detectors. In further examples, multiple light sources or input fibers could be employed to emit PDWs into tissue 360, but be positioned on tissue 360 at different distances from a common detector or common detection fiber, where multiple input fibers and a single detector or detection fiber could be employed. Likewise, in other examples, a single light source or input fiber could be employed to emit a PDW or PDWs into tissue 360, while multiple detectors or detection fibers are positioned at different distances along tissue 360 from the input.

In yet further examples, the laser light from each of lasers 324-325 is multiplexed or combined onto a single optical fiber. In examples using a single optical fiber to carry multiple optical signals, the multiplexed signals could be time-division multiplexed (TDM), such as when RF switch 322 alternately provides the modulation signal to lasers 324-325, or wavelength-division multiplexed (WDM), such as when RF switch 322 simultaneously provides the modulation signal to lasers 324-325. Frequency-division multiplexing (FDM) could also be employed, where different modulation frequencies are used for each of lasers 324-325. The PDW signals from both lasers could be mixed or combined onto a single optical fiber for emission into tissue 360. Detectors 330-331 could also share a single optical fiber, and perform frequency separation to distinguish the different modulation frequencies of the PDW signals. A single detector could also be employed to detect multiple PDW signals, or to share multiple detection optical fibers. Two optical fibers could also be employed for detection of the PDW signals at different distances on tissue 360, and frequency separation could be performed in each of detectors 330-331 to determine PDW signals for each modulation frequency. Other configurations could be employed, such as code-division multiplexing (CDM), where additional code-based modulation on the optical signals is employed to create code-separated channels. Frequency hopping, chirping, or spread spectrum techniques could also be employed.

Figure 4:
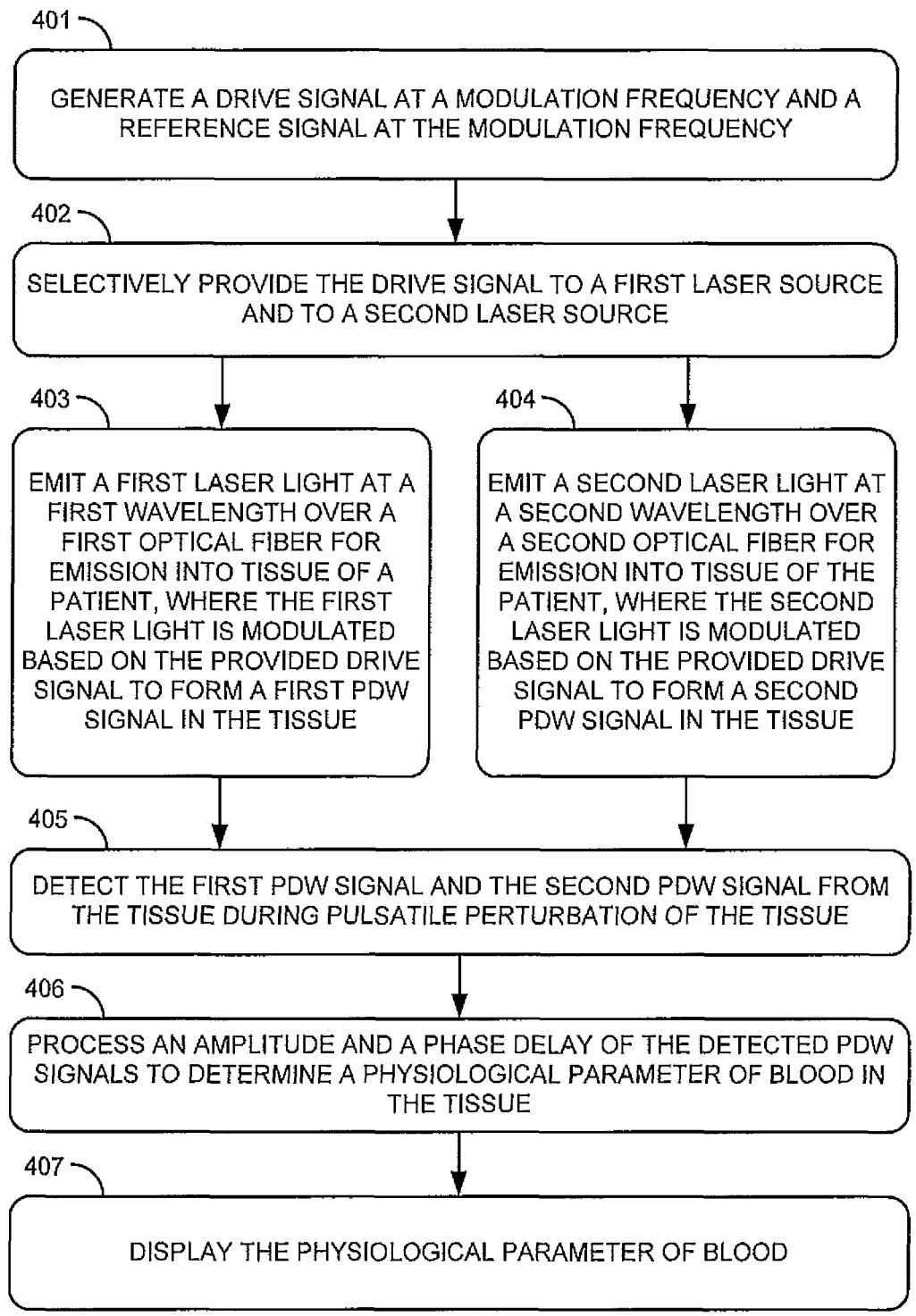
FIG. 4 is a flow diagram illustrating a method of operation of a system for measuring a physiological parameter of blood in a patient.

FIG. 4 is a flow diagram illustrating a method of operating system 300 for measuring a physiological parameter of blood in a patient. The operations of FIG. 4 are referenced herein parenthetically. In FIG. 4, signal synthesizer 320 generates (401) a drive signal at a modulation frequency and a reference signal at the modulation frequency. The drive signal is then provided to RF switch 322 over link 341, and the reference signal is provided to PA detector 332 over link 342. Signal synthesizer 320 receives instructions over link 340 from processing module 310 for generating the drive and reference signals. In this example, the instructions include instructions for a modulation frequency, amplitude, and phase delay for the drive signal and the reference signal. A calibration process could be performed to adjust the modulation frequency, amplitude, and phase delay for the drive signal and the reference signal The modulation frequency of the drive and reference signals could be selected according to properties of tissue 360 and the blood contained therein. At high modulation frequencies, a photon density wave (PDW) will be created in tissue 360 and propagate through the tissue, being scattered by tissue 360 and blood particles in tissue 360. The modulation frequency is typically selected between 100 MHz and 3000 MHz, although other frequencies could be selected. In one embodiment, a 400 MHz modulation frequency is selected. A specific modulation frequency could be selected to provide good resolution in operation 406, such as to increase fidelity of a measured phase delay of a detected PDW signal after propagation through tissue 360. In another example, the modulation frequency may be increased over time until the phase delay detected in operation 406 is large enough for processing of the physiological parameter, such as crossing a phase delay detection threshold.

The phase delay between the drive and reference signals is selected as a predetermined delay, to allow PA detector 332 to determine a phase delay between the detected signals received over links 374-374 and the reference signal provided over link 342. The phase delay could be adjusted to compensate for variable delays in cable lengths, propagation times, processing and detection times of the drive signal or PDW signals. In this example, the phase delay can be selected independently of the amplitude of the drive and reference signals. A digital signal synthesis device is used, such as a DDS device, to allow for independent adjustment between amplitude and phase at a particular modulation frequency for the drive and reference signals. As further examples, the phase delay between the drive and reference signals could be zero, or the drive and reference signals could be phase locked.

The amplitudes of the drive and reference signals are selected according to the linear ranges of PA detector 332 and of detectors 330-331, as well as to possibly compensate for attenuation experienced by the drive or reference signals when propagating through the various elements of measurement device 380. Feedback monitoring is employed to ensure that amplitudes of detected PDW signals fall within a predetermined input range of PA detector 332 or of detectors 330-331. If the amplitude of the detected PDW signals is too low, such as when a signal-to-noise level of the PDW is too low, or the amplitudes of the detected PDW signals fall outside of a linear input range for PA detector 332 or of detectors 330-331, the amplitude of the drive and reference signals could then be increased. Likewise, the amplitude for the drive and reference signals could be decreased if the amplitudes of the detected PDW signals exceed a linear input range for PA detector 332 or of detectors 330-331, or if clipping occurs on the inputs of PA detector 332 or of detectors 330-331. It should be understood that the amplitudes for the drive and reference signals could be adjusted independently and to different values. In some examples, multiple drive signals are generated and provided to RF switch 322, where the multiple drive signals comprise different amplitudes, phases, or modulation frequencies.

In one embodiment, the phase delay and the amplitude are transferred to a comparator or a low resolution ADC where they are compared to a nominal value, such as a midpoint of an output range of PA detector 332. Processing module 310 may then adjust the drive current (such as amplitude and phase delay) until the midpoint is reached. In this manner, the settings for signal synthesizer 320 are actually the desired output rather than of the comparator or low resolution ADC which are then used for control. Furthermore, the output range of PA detector 332 may be expanded in order to lower noise contribution of its output signal. In another embodiment, processing module 310 sets the reference signal amplitude to a predetermined value, such as a −10 dBm level when measured at the input of PA detector 332. Using the output of PA detector 332, processing system 310 also can adjust the light source drive signal, such as amplitude, bias, and PA detector 332 provides output signals in a linear part of the output range of PA detector 332. In further examples, a different phase and amplitude of the drive signal is used for each laser, such as when four lasers are used. Profiles could be selected between in signal synthesizer 320 to select which phase and amplitude configuration is presently desired for the drive signal, and the profiles could be selected according to which laser is activated, in a synchronous manner. In another example, amplitudes and phase delays of the drive signal or reference signal are adjusted so that small steps are seen by PA detector 332 when switching between lasers to allow for fast setting times, quick detection transitions, and rapid filtering adjustments.

RF switch 322 selectively provides (402) the drive signal to a first laser source and to a second laser source. The first laser source is laser 324 and the second laser source is laser 325. In this example, RF switch 322 alternately provides the drive signal to laser 324 and laser 325, over associated links 343-344. The switching rate for RF switch 322 could be provided by processing module 310, or set to a predetermined rate. For example, a 50% duty cycle could be employed on RF switch 322 to provide the drive signal to each of laser 324 and laser 325. In other examples, RF switch 322 incorporates on 'off' period where the drive signal is not provided to either of laser 324 and laser 325. In further examples, RF switch 322 only provides the drive signal to laser 324 or laser 325 when a measurement is occurring; otherwise the drive signal is not provided to laser 324 or laser 325. Processing module 310 can control the activation of each of lasers 324-325, for instance to power up an individual laser, wait until a measurement has been taken, and then power down the laser. In one example, such as when using four laser sources, each laser may have a duty cycle of 25% or 2.5 ms, giving an overall sample or measurement rate of 100 Hz for each of the four laser output signals. Other sample rates are possible including where each laser is powered on for a shorter period of time than a 25% duty cycle, and remain powered off when not activated.

Laser 324 emits (403) a first laser light at a first wavelength over first optical fiber 371 for emission into tissue 360 of the patient, where the first laser light is modulated based on the provided drive signal to form a first photon density wave (PDW) signal in tissue 360. Laser 325 emits (404) a second laser light at a second wavelength over second optical fiber 372 for emission into tissue 360 of the patient, where the second laser light is modulated based on the provided drive signal to form a second PDW signal in tissue 360. The first wavelength and the second wavelength represent the wavelength of the light emitted by the laser. In this example, the first wavelength is 660 nanometers (nm) and the second wavelength is 808 nm, although other wavelengths could be employed. The wavelengths are selected in typical examples to be absorbed by or be scattered by specific particles or constituents of the blood or tissue 360. In some examples, multiple wavelengths are employed to reduce sensitivity of the measurements to patient-specific properties, such as skin type, age, melanin content, or other properties. Modulation of the laser light at high frequencies, such as 100-1000 MHz, causes resolvable photon density waves to propagate through tissue 360. The modulation signal could comprise a sine wave of the particular modulation frequency, and lasers 324-325 each mix or combine the modulation signal with the associated laser light to create a modulated optical signal, such a PDW. Other waveforms could be employed by signal synthesizer 320, such as square waves, sawtooth waves, or arbitrary waveforms.

Detectors 330-331 detect (405) the first PDW signal and the second PDW signal from tissue 360 during pulsatile perturbation of tissue 360. The first PDW and the second PDW are propagated into tissue 360 via optical fibers 371-372. The light signatures of both the first PDW and the second PDW are received into optical fibers 373-374 for transfer to detectors 330-331. In this example, each of optical fibers 373-374 receives the light signatures from both the first PDW and the second PDW. Detectors 330-331 convert the optical signals received over the associated optical fibers 373-374 into electrical signals. Detectors 330-331 could also process the optical or electrical signals to remove laser bias, or recondition noisy signals, among other operations. Detectors 330-331 transfer the electrical representations of the detected signals to PA detector 332 over links 350-351. It should be understood that the signal carried over link 350 represents a first combination of the first PDW signal and the second PDW signal, and the signal carried over link 351 represents a second combination of the first PDW signal and the second PDW signal. The pulsatile perturbation of tissue 360 includes a vascular palpitation induced by the heart of the patient, although other pulsatile perturbations could be employed. Characteristics of the pulsatile perturbation include time-based characteristics of the pulsatile perturbation, such as volumetric changes over time of tissue 360. For example, the characteristics of the received photon density waves may be time varying, such as when the heart of the patient ejects blood and the number of absorbing and scattering particles between the emitted photon density waves and detected photon density waves is greater at some points in the cardiac cycle than others.

Processing module 310 processes (406) an amplitude and a phase delay of the detected PDW signals to determine a physiological parameter of blood in tissue 360. The physiological parameter could include any parameter associated with blood or tissue 360 of the patient, such as total hemoglobin concentration (tHb), regional oxygen saturation (rSO2), or arterial oxygen saturation (SpO2), among other parameters, including combinations thereof. The amplitude and the phase delay of the detected PDW signals can change during pulsatile perturbation of tissue 360. These changing signals are processed with pulsatile perturbation characteristics to determine a value of the physiological parameter. In typical examples, the pulsatile perturbation introduces dynamic, quasi-periodic, or "AC" information into the amplitude and the phase delay of the detected PDW signals, and the dynamic amplitude and phase delay of the detected PDW signals could be processed to determine a value of the physiological parameter. For example, the pulsatile perturbation characteristics could provide an AC amplitude and AC phase delay for each of the plurality of photon density waves, which are then processed to determine a value of the physiological parameter. Time-averaged characteristics, such as "DC" information, could also be taken into account. The amplitude and phase delay of the detected PDW signals could be represented by a pulsatile waveform of the characteristics of the plurality of photon density waves, such as a photoplethysmograph (PPG) including the amplitudes or the phase delays over a predetermined timeframe, although other representations could be employed.

In systems with one light source and one detector, four signals can be determined, namely AC and DC phase delays, and AC and DC amplitudes. In systems with more light sources and detectors, more signals can be determined accordingly. The multiple signals are determined by using the properties of the pulsatile changes to extract both AC and DC information, Phase variations are typically induced by pulsatile changes in scattering of light due to changes in blood volume in the probed volume or tissue, such as PDW transmission pathlength changes over the pulsatile perturbation. The variation in AC scattering to DC scattering measured by phase delay can Yield information about the total arterial volume probed. The resulting change in AC amplitude and DC amplitude can yield information about the absorption in the volume. The AC and DC amplitude and phase delays processed together can yield the total hemoglobin per unit volume.

In further examples, the received signals detected by detectors 330-331 are downconverted to an intermediate frequency (IF) using common communication system tuner techniques, such as heterodyning. A combined programmable gain block and downconversion block may be found in many commodity components and devices. The baseband or IF signals could then be directly digitized and transferred to processing module 310 which calculates amplitude and phase delays instead of a discrete PA detector. A wider range of input phase relationships could be handled in this manner. In IF examples, ADC 324-325 must have sufficient bandwidth to sample the IF rather than the baseband phase and amplitude signals, and PA detector 332 could be replaced by a mixer or radio tuner circuit. Downconverting to IF and digitizing can have advantages over some example PA detectors, such as an AD8302, because certain PA detector circuitry may not perform well at certain phase differences between the input and reference signal and require more precise control of phase and amplitude inputs.

A cross correlation between the reference signal and the received PDW signals could be used to calculate phase delay in processing module 310. Amplitude could be determined by comparing signal power. Digital filtering or conditioning could be performed on the signals prior to determination of amplitude or phase delay. In yet further examples, processing module 310 may also determine physiological parameters from the raw signals determined by detectors 330-331, or the offset (DC) or time varying (AC) components of the phase and amplitude signals instead of a discrete PA detector. Processing module 310 may also evaluate signal quality and ambient noise and vary the drive or reference signal power, waveform shape, or frequency to increase the signal-to-noise ratio of the signals.

During calibration and test processes, processing module 310 may directly drive the reference signal to PA detector 332, which may be buffered, amplified, or conditioned prior to use by PA detector 332. Calibration typically includes as many intermediate components as possible used in the final measurement configuration. During self-test, processing module 310 could generate known combinations of drive and reference signals and measure the phase delay and amplitudes of both. For calibration, processing module 310 could characterize non-linearity or errors of these signals after each power up of measurement device 380, or done one time and stored in a non-transitory computer readable medium. System 300 may also include a loopback cable internal or external to measurement device 380, which feeds laser signals back to detectors 330-331 without transmission through tissue 360. Clamp assembly 370 could also be attached to a test sample, such as a Teflon reference tissue, or other representative model to test or calibrate measurement device 380. Specialized clamp assemblies may be used which incorporate different delay elements or attenuation portions to simulate different tissue properties, or to aid in calibration of different parameters, such as phase delay or amplitude variations due to different optical fiber lengths or other optical component variations.

Once the physiological parameter is determined, then user interface 312 displays (407) the physiological parameter of the blood of the patient. User interface 312 could include a graphical user interface, and display the physiological parameter on the graphical user interface, and may include numerical data, graphs, charts, or other information. The physiological parameter could also be transferred for use in other devices or systems, or transferred to a database computer system for compilation with other patient data. A physical printout of the physiological parameter could also be provided. In one example, processing module 310 controls a display, which could be associated with user interface 312, and interprets user control signals to implement a user interface. In other examples, processing module 310 communicates with a server or host processor for data storage and control. Processing module 310 may include a host interface which may communicate over a UART, serial port, USB, wireless link, network, or Ethernet connection, among other interfaces, and may include protocols such as Nellcor SHIP, among others.

As discussed above, the phase delay of a PDW is sensitive to changes in the scattering properties or scattering coefficient of the measured tissue, whereas the amplitude of a PDW is sensitive to concentrations of an absorber in the measured tissue or to absorption coefficient. Tissue beds, such as tissue 360 are typically treated as a homogenous mixture of blood and other tissues containing no blood. The pulsatile perturbation naturally causes perfusion of the blood through tissue 360. In general terms, the ratio of the differentials of the PDW amplitudes to the phase delay signals is a linear function of the absorption coefficient of the probed tissue, and can be used to derive the total hemoglobin concentration (tHb) measurement. In this example, the pulsatile perturbation introduces a small perturbation into this measurement, and the phase delay and amplitude are affected by the pulsatile perturbation to create dynamic or "AC" values for phase delay and amplitude. The ratio of the differential of the amplitude and phase delay can approximated as the ratio of the AC amplitude over the AC phase delay, such that the coefficient of absorption is proportional to the AC amplitude over the AC phase, which is shown below (equations are numbered for convenience):

$$\frac{dA/d\mu_a}{d\varphi/d\mu_a} \approx \frac{A_{ac}}{\varphi_{ac}} \propto \mu_a \tag{0a}$$

Where $\mu_a$ represents the absorption coefficient. For isosbestic wavelength choices, such as 808 nm in this example, tHb can be determined by:

$$\frac{A_{ac}}{\varphi_{ac}} \propto \mu_a = tHb \times \varepsilon_{808} \tag{0b}$$

Where $\varepsilon_{808}$ represents the molar extinction coefficient of the blood in tissue 360 at 808 nm. Upon determining $\mu_a$, various physiological parameters, including tHb, rSO2, SpO2, or others, may be calculated.

Alternatively, a multi-distance PDW DC measurement, in which the pulsatile perturbation may be ignored, may be used to determine the desired physiological parameters. A detailed analysis now follows. The optical properties of tissue 360 can be determined by:

$$\mu_a = V_{art}\mu_{a,art} + V_{ven}\mu_{a,ven} + (1 - V_{art} - V_{ven})\mu_{a,tiss} \tag{1a}$$

$$\mu'_s = (V_{art} + V_{ven})\mu'_{s,b}(1 - V_{art} - V_{ven})\mu'_{s,tiss} \tag{1b}$$

Where $V_{art}$, $V_{ven}$ are the volume fractions of arterial and venous blood, respectively, and $\mu_a$ is the absorption coefficient and $\mu'_s$ represents the scattering coefficient.

During the perfusion, the optical properties of the tissue beds change as blood volume increases, so Eq (1a) and (1b) become:

$$\mu_{a,p} = V_{art}\mu_{a,art} + V_{ven}\mu_{a,ven} + (1 - V_{art} - V_{ven})\mu_{a,tiss} + \tag{2a}$$
$$\Delta V_{art}(\mu_{a,art} - \mu_{a,tiss})$$
$$= \mu_{a,DC} + \Delta V_{art}(\mu_{a,art} - \mu_{a,tiss})$$

$$\mu'_{s,p} = (V_{art} + V_{ven})\mu'_{s,b} + (1 - V_{art} - V_{ven})\mu'_{s,tiss} + \tag{2b}$$
$$\Delta V_{art}(\mu'_{s,b} - \mu'_{s,tiss})$$
$$= \mu'_{s,DC} + \Delta V_{art}(\mu'_{s,b} - \mu'_{s,tiss})$$

Where $\Delta V_{art}$ is the volume fraction change of arterial blood due to perfusion.

Under a semi-infinite boundary condition, such as finger tips, when $r(3\mu_a\mu'_s)^{1/2} \gg 1$, the measurements using a PDW system can be given as the following:

$$\ln(R_{DC}r) = -r(\mu_a/D)^{1/2} + R_{DC}(D, K_{DC}) \tag{3a}$$

$$\Phi = r\left(\frac{\mu_a}{2D}\right)^{1/2}\left\{\left[1+\left(\frac{\omega}{v\mu_a}\right)^2\right]^{1/2}-1\right\}^{1/2} + \Phi'_{DC}(K_\Phi) \quad (3b)$$

Where r is the distance between the emitter and the receiver, $R_{DC}$ is the reflectance, $\Phi$ is the phase shift, D is the diffusion constant=$1/(3\mu_a+3\mu'_s)$ (approximately $\frac{1}{3}\mu'_s$ at wavelengths typically used for oximetry), $\omega$ is the laser modulation frequency, v is the speed of light in tissue.

The constant offset terms $R_{DC}(D,K_{DC})$ and $\Phi'_{DC}(K_\Phi)$ are determined by D and instrumental factors. $K_\Phi$ is the relative phase of the source plus any phase shifts external to the tissue. Further details on obtaining Eq. (3a) are shown further below.

So for a two-distance PDW measurement, one can obtain:

$$\Delta R_A = -(r_2-r_1)\sqrt{\mu_a/D} \quad (4a)$$

$$\Delta\Phi = \Phi_2 - \Phi_1 = (r_2-r_1)\left(\frac{\mu_a}{2D}\right)^{1/2}\left\{\left[1+\left(\frac{\omega}{v\mu_a}\right)^2\right]^{1/2}-1\right\}^{1/2} \quad (4b)$$

The tissue optical properties can then be calculated as the following. By taking the ratio of Eq. (4b) to (4a), one obtains:

$$\Delta\Phi/\Delta R_A = -(1/2)^{1/2}\left\{\left[1+\left(\frac{\omega}{v\mu_a}\right)^2\right]^{1/2}-1\right\}^{1/2} \quad (5)$$

Therefore, the absorption coefficient $\mu_a$ can be calculated as:

$$\mu_a = \frac{\omega}{v}\frac{1}{\{[2(\Delta\Phi/\Delta R_A)^2+1]^2-1\}^{1/2}}. \quad (6)$$

For a high modulation frequency ($2\pi f \gg \mu_a v$), phase $\Phi$ can be simplified to:

$$\Phi = r\left(\frac{\omega}{vD}\right)^{1/2} + \Phi'_{DC}(K_\Phi) \quad (6a)$$

So Eq. (6) can be simplified as:

$$\mu_a = \frac{\omega}{v}\frac{1}{(\Delta\Phi/\Delta R_A)^2} \quad (6b)$$

Having calculated $\mu_a$, one can now calculate $\mu_s$ per equation (4a) or (4b), Per (4a), $$\mu'_s = \frac{(\Delta R_A)^2}{3\mu_a(r_2-r_1)^2} - \mu_a \quad (7a)$$

Per (4b), $$\mu'_s = \frac{(\Delta\Phi)^2}{1.5\mu_a(r_2-r_1)^2\left\{\left[1+\left(\frac{\omega}{v\mu_a}\right)^2\right]^{1/2}-1\right\}} - \mu_a \quad (7b)$$

By choosing two equal minimal flow-rate points, $t_1$ and $t_2$, on the measured PPG waveforms, one can obtain from (2a):

$$\Delta V_{art}\mu_{a,art} = \mu_{a,t2} - \mu_{a,t1} = x, \quad (8)$$

Where $\Delta V_{art}$ is the volume fraction change of the arterial blood due to perfusion, and $$x = \frac{\omega}{v}\frac{1}{\{[2(\Delta\Phi_{t2}/\Delta R_{A,t2}r)^2+1]^2-1\}^{1/2}} - \frac{\omega}{v}\frac{1}{\{[2(\Delta\Phi_{t1}/\Delta R_{A,t1})^2+1]^2-1\}^{1/2}}. \quad (9)$$

$$\mu_{a,art} = C_{ox}\varepsilon_{ox}(\lambda) + C_h\varepsilon_h(\lambda)$$

Where $\mu_{a,tiss}$ is ignored, and $C_{ox}$, $C_h$ are the concentrations of the oxy-hemoglobin and deoxyhemoglobin, respectively. Substituting Eq (9) into Eq (8), one obtains:

$$\Delta V_{art}[C_{ox}\varepsilon_{ox}(\lambda)+C_h\varepsilon_h(\lambda)]=x(\lambda) \quad (9a)$$

Likewise, from (2b) $\lambda'_s$ one obtains:

$$\Delta V_{art}(\mu'_{s,b} - \mu'_{s,tiss}) = \mu'_{s,t2} - \mu'_{s,t1} = y(\lambda), \quad (10)$$

$$\text{Where } y = \frac{\left(\frac{(\Delta R_{A,t2})^2}{3\mu_{a,t2}} - \mu_{a,t2}\right) - \left(\frac{(\Delta R_{A,t1})^2}{3\mu_{a,t1}} - \mu_{a,t1}\right)}{(r_2-r_1)^2}$$

Dividing (10) by (9a) cancels $\Delta V_{art}$, yielding:

$$\frac{y_\lambda}{x_\lambda} = z_\lambda = \frac{\mu'_{s,b}(\lambda) - \mu'_{s,tiss}(\lambda)}{C_{ox}\varepsilon_{ox}(\lambda) + C_h\varepsilon_h(\lambda)} \quad (11)$$

$$z_\lambda\varepsilon_{ox,\lambda}C_{ox} + z_\lambda\varepsilon_{h,\lambda}C_h - \mu'_{s,b,\lambda} + \mu'_{s,tiss,\lambda} = 0$$

In Eq. (11), there are four un-knows, namely the reduced scattering coefficients for blood and tissue, and the blood concentrations of oxy- and deoxy-hemoglobin, assuming that values of $\lambda$ are selected such that all $\mu'_{s,b,\lambda}$ are essentially equal. Therefore, four equations will be required to obtain the desired parameters. This can be achieved by using a four-wavelength system. Assuming that $\mu'_{s,tiss,\lambda}$ is essentially equal to $\mu'_{s,\lambda}$ reduces (11) to three unknowns and three wavelengths. However, for a dual-wavelength PDW system as the one shown in FIG. 3, the SpO2 measurement afforded by the PPG waveforms can be used as one of equations to solve the problem given that:

$$SpO2 = C_{ox}/(C_{ox}+C_h) = C_{ox}/C_{art}$$

$$\varepsilon_{art,\lambda} = SpO2\varepsilon_{ox,\lambda} + (1-SpO2)\varepsilon_{h,\lambda}$$

$$z_\lambda\varepsilon_{art,\lambda}(C_{ox}+C_h) - \mu'_{s,b,\lambda} + \mu'_{s,tiss,\lambda} = 0 \quad (12)$$

Total hemoglobin concentration may be calculated directly from $(C_{ox}+C_h)$. The term $\mu'_{s,b,\lambda}$ should vary as a roughly parabolic function of hematocrit, and be monotonically increasing between 0% and approximately 50% hematocrit, and may therefore be used to estimate either hemoglobin or hematocrit over most of the clinically relevant range. Discrepancies between these two methods of estimating blood hemoglobin may be indicative of certain anemias, perturbations in cell size, or coagulopathies. So with a dual wavelength PDW system, rSO2, SpO2 and total hemoglobin concentration can be obtained simultaneously.

It should be understood that various empirically adjustments may be required in order to optimize the accuracy of calculations based on the above equations. Factors such as finite tissue, emitter, and detector dimensions, or microvascular dilution due to the Fahreus effect, may impose a linear or non-linear mapping between theoretical estimates of blood hemoglobin or hematocrit and actual clinical values. Likewise, the simplifying assumptions introduced with regard to the relationship between reduced scattering coefficients may be refined to assume a predictable, but unequal, relationship between scattering coefficients at multiple wavelengths, and between estimated and bloodless tissue scattering. For SpO2, the phase measurement enables to dynamically compensate the pathlength mismatch errors in different saturation scenarios, yielding better accuracy in wider saturation range.

Figure 5:
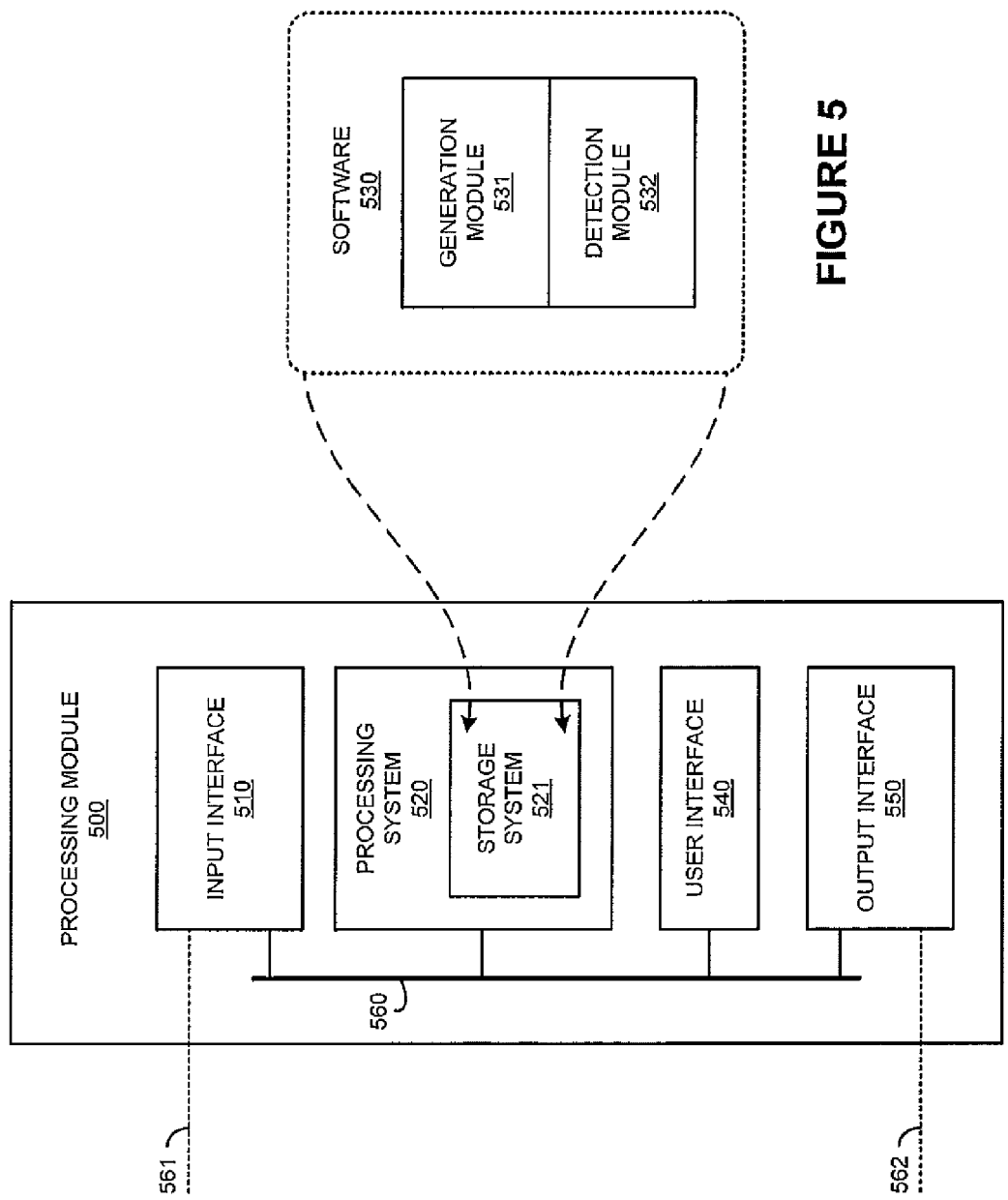
FIG. 5 is a block diagram illustrating a processing module.

FIG. 5 is a block diagram illustrating processing module 500, as an example of processing module 110 found in FIG. 1 or processing module 310 found in FIG. 3, although processing module 110 or processing module 310 could use other configurations. Processing module 500 includes, input interface 510, processing system 520, user interface 540, and output interface 550. Input interface 510, processing system 520, user interface 540, and output interface 550 are shown to communicate over a common bus 560 for illustrative purposes. It should be understood that discrete links could be employed, such as network links or other circuitry. Processing module 500 may be distributed or consolidated among equipment or circuitry that together forms the elements of processing module 500. In some examples, user interface 540 is not included in processing module 500.

Input interface 510 comprises a communication interface for communicating with other circuitry and equipment, such as with receiver module 130, user interface 312, or ADC 334-335. Input interface 510 could include transceiver equipment exchanging communications over the associated link 561. It should be understood that input interface 510 could include multiple interfaces, pins, transceivers, or other elements for communicating with multiple external devices. Input interface 510 also receives command and control information and instructions from processing system 520 or user interface 540 for controlling the operations of input interface 510. Link 561 could use various protocols or communication formats as described herein for links 170-171, 340-344, or 350-356, including combinations, variations, or improvements thereof.

Processing system 520 includes storage system 521. Processing system 520 retrieves and executes software 530 from storage system 521. In some examples, processing system 520 is located within the same equipment in which input interface 510, user interface 540, or output interface 550 are located. In further examples, processing system 520 comprises specialized circuitry, and software 530 or storage system 521 could be included in the specialized circuitry to operate processing system 520 as described herein. Storage system 521 could include a non-transitory computer-readable medium such as a disk, tape, integrated circuit, server, flash memory, or some other memory device, and also may be distributed among multiple memory devices.

Software 530 may include an operating system, logs, utilities, drivers, networking software, tables, databases, data structures, and other software typically loaded onto a computer system. Software 530 could contain application programs, server software, firmware, processing algorithms, or some other form of computer-readable processing instructions. When executed by processing system 520, software 530 directs processing system 520 to operate as described herein, such as instruct transmission modules on signal modulations, receive characteristics of PDWs, process the characteristics of PDWs to determine blood parameters, among other operations.

In this example, software 530 includes generation module 531 and detection module 532. It should be understood that a different configuration could be employed, and individual modules of software 530 could be included in different equipment in processing module 500. Generation module 531 determines modulation parameters for use by a transmission module or signal synthesis circuitry, such as modulation frequency, phase delay for reference signals, laser activation periods, TDM, FDM, or CDM parameters, among other operations. Detection module 532 receives receive characteristics of PDWs as detected by external circuitry, and processes the characteristics of the PDWs to determine blood parameters, among other operations. Detection module 532 could receive reference signals from a transmission module or signal synthesis circuitry for processing with the characteristics of the PDWs.

User interface 540 includes equipment and circuitry to communicate information to a user of processing module 500. Examples of the equipment to communicate information to the user could include displays, indicator lights, lamps, light-emitting diodes, haptic feedback devices, audible signal transducers, speakers, buzzers, alarms, vibration devices, or other indicator equipment, including combinations thereof. The information could include blood parameter information, waveforms, summarized blood parameter information, graphs, charts, processing status, or other information. User interface 540 also includes equipment and circuitry for receiving user input and control, such as for beginning, halting, or changing a measurement process or a calibration process. Examples of the equipment and circuitry for receiving user input and control include push buttons, touch screens, selection knobs, dials, switches, actuators, keys, keyboards, pointer devices, microphones, transducers, potentiometers, non-contact sensing circuitry, or other human-interface equipment.

Output interface 550 comprises a communication interface for communicating with other circuitry and equipment, such as with transmission module 120, signal synthesizer 320, or user interface 312. Output interface 550 could include transceiver equipment exchanging communications over the associated link 562. It should be understood that output interface 550 could include multiple interfaces, pins, transceivers, or other elements for communicating with multiple external devices. Output interface 550 also receives command and control information and instructions from processing system 520 or user interface 540 for controlling the operations of output interface 550. Link 562 could use various protocols or communication formats as described herein for links 170-171, 340-344, or 350-356, including combinations, variations, or improvements thereof.

Bus 560 comprises a physical, logical, or virtual communication link, capable of communicating data, control signals, and communications, along with other information. In some examples, bus 560 is encapsulated within the elements of processing module 500, and may be a software or logical link. In other examples, bus 560 uses various communication media, such as air, space, metal, optical fiber, or some other signal propagation path, including combinations thereof. Bus 560 could be a direct link or might include various equipment, intermediate components, systems, and networks.

Figure 6:
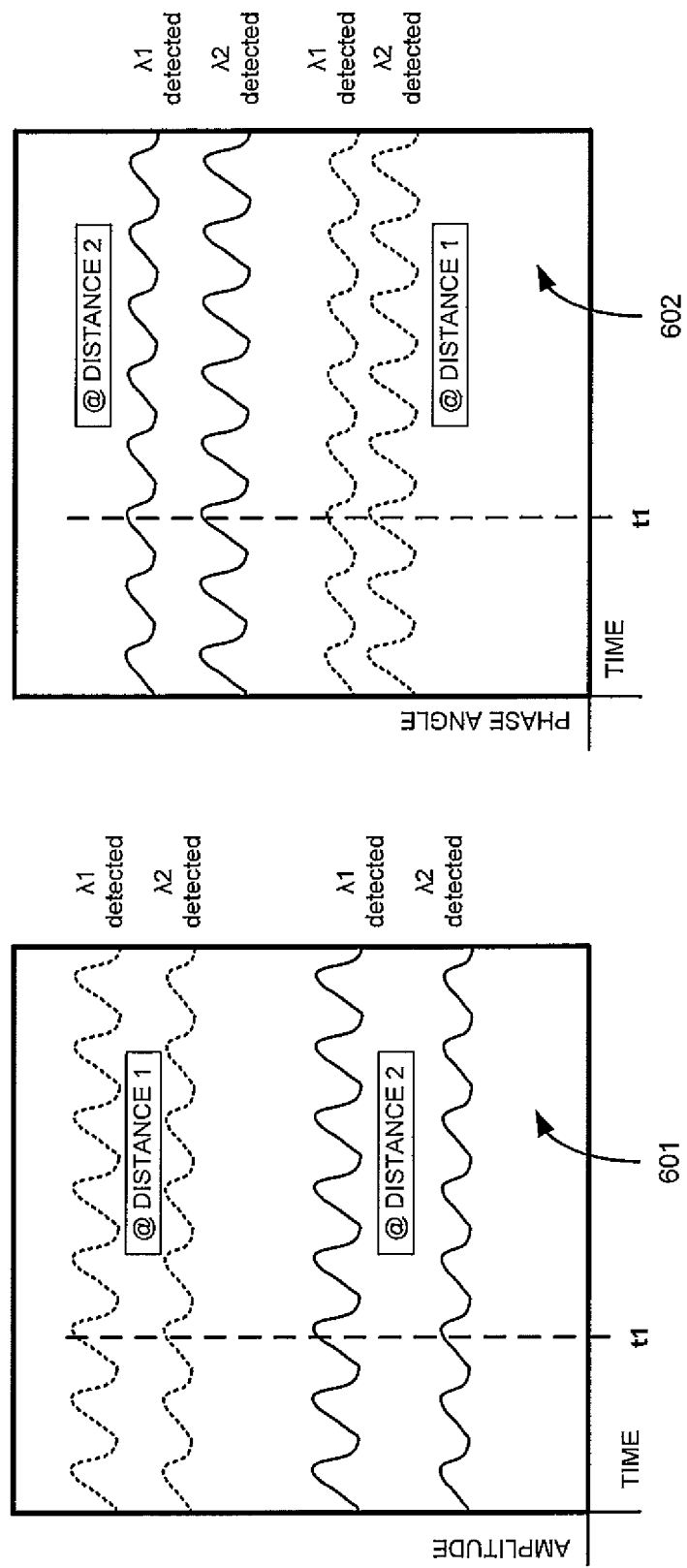
FIG. 6 includes two graphs illustrating example parameter measurements.

FIG. 6 includes graph 601 and graph 602 illustrating example parameter measurements for system 300 shown in FIG. 3. Graphs 601 and 602 are representative photoplethysmographs (PPG) of tissue 360. In graph 601, amplitudes of PDW signals are shown over time, with an upper group of waveforms detected by detector 330 over optical fiber 373 at distance 1, and a lower group of waveforms detected by detector 331 over optical fiber 374 at distance 2. As discussed herein, each optical fiber 373-374 will detect both the first PDW and the second PDW. Accordingly, two wavelengths of PDWs are shown for each distance in graph 601, namely wavelength 1 (λ1) emitted by laser 324 and wavelength 2 (λ2) emitted by laser 325. The vertical axis of graph 601 represents amplitude, and could be shown in units of intensity, power, or other amplitude property of the PDWs. The horizontal axis of graph 601 represents time.

In graph 602, phase angles of PDW signals are shown over time, with an upper group of waveforms detected by detector 331 over optical fiber 374 at distance 2, and a lower group of waveforms detected by detector 330 over optical fiber 373 at distance 1. As discussed herein, each optical fiber 373-374 will detect both the first PDW and the second PDW. Accordingly, two wavelengths of PDWs are shown for each distance in graph 602, namely wavelength 1 (λ1) emitted by laser 324 and wavelength 2 (λ2) emitted by laser 325. The vertical axis of graph 602 represents phase angle, and could be shown in units of degrees, radians, or other unit of the phase angle. The horizontal axis of graph 602 represents time. Detectors 330-331 would not typically detect phase delays between detected PDWs, only amplitudes or intensities. Therefore, the phase angle graph 602 would be typically produced after processing by PA detector 332 or processing module 310.

The quasi-periodic amplitude and phase angle variations seen in graphs 601 and 602 are primarily induced by pulsatile perturbations of tissue 360, with each peak-valley cycle representing an individual pulsatile perturbation, such a cardiac cycle. Also, as the PDW signals introduced into tissue 360 are comprised of modulated light, the waveforms shown in each of graphs 601 and 602 may also reflect this modulation, but the modulation frequency is much higher than the pulsatile perturbation rate. For example, the heart rate or associated pulsatile perturbation may be around 1 Hz, whereas the modulation frequencies of the PDWs could be 100-1000 MHz. Therefore, the modulation information is not reflected in graphs 601 and 602. A time indicator, namely t1, is shown in both graph 601 and 602, and will be used to discuss more detailed analysis of the waveforms in FIG. 7.

Figure 7:
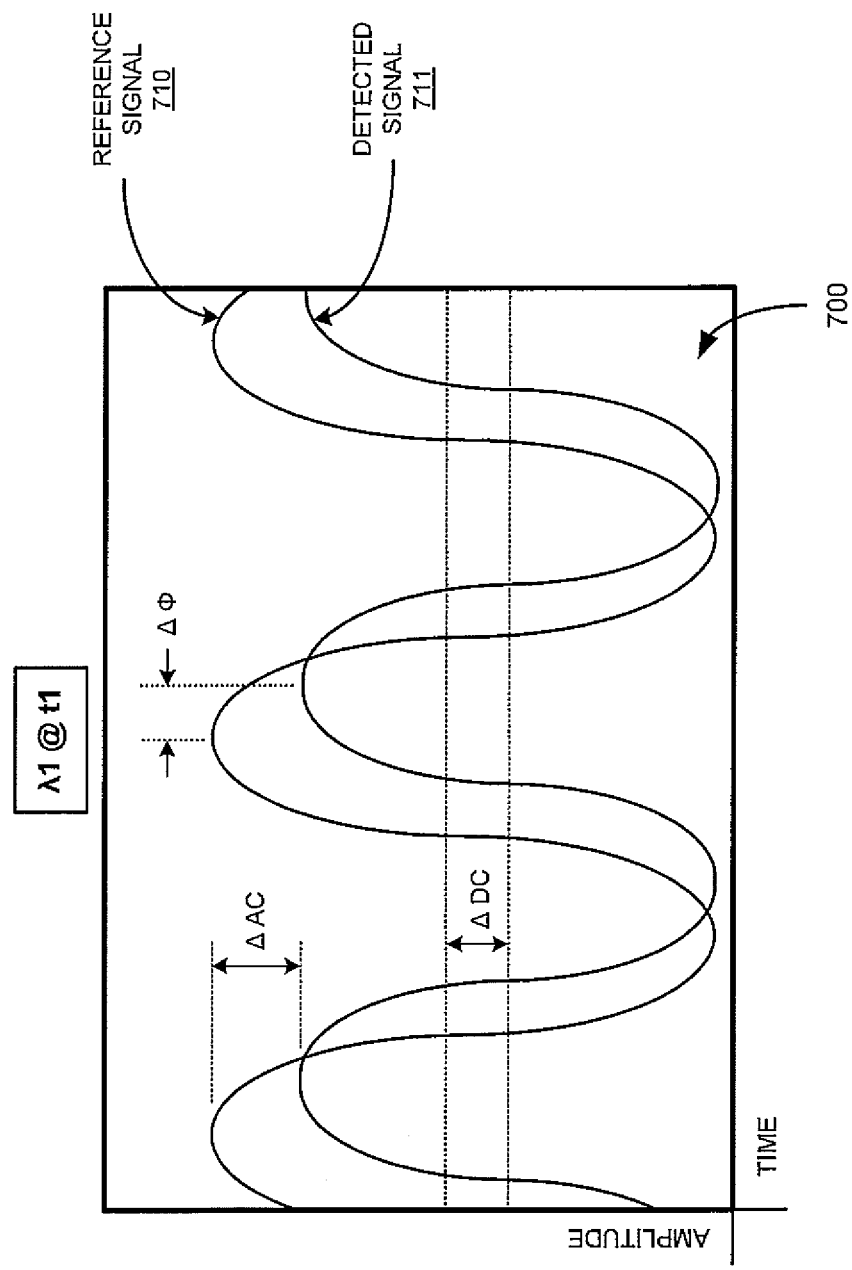
FIG. 7 includes a graph illustrating example parameter measurements.

FIG. 7 includes graph 700 illustrating example parameter measurements. Graph 700 could represent a snapshot of the graphs of FIG. 6 at time t1, at a highly zoomed or magnified timeframe. Specifically, the PPG waveforms of FIG. 6 could be represented in graph 700, where detected signal 711 comprises a magnified portion of one of the amplitude waveforms for wavelength 1 or wavelength 2, at a selected distance 1 or distance 2 at time t1. The oscillations seen in graph 700 represent the high frequency modulation of the associated detected PDW signal and reference signal, and do not represent pulsatile perturbations. Reference signal 710 and detected signal 711 are shown in graph 700. Reference signal 710 is an example reference signal provided to PA detector 332, whereas detected signal 711 is an example of any of the detected PDW signals detected by either of detectors 330-331 and provided to PA detector 332.

As shown in graph 700, a delta in the peaks of reference signal 710 and detected signal 711 is indicated by Δ AC, or a dynamic differential in amplitude between reference signal 710 and detected signal 711. A delta in the average values of reference signal 710 and detected signal 711 is indicated by Δ DC, or a static differential in amplitude between reference signal 710 and detected signal 711. A delta in the phase of reference signal 710 and detected signal 711 is indicated by Δ Φ, or a dynamic differential in phase delay between reference signal 710 and detected signal 711. For determining phase delay, reference signal 710 is used as a baseline, and the timewise shift in detected waveform 711 from reference signal 710 is indicative of the phase delay. These various deltas can be determined by PA detector 332 or processing module 310, and processed to determine the physiological parameters as discussed herein.

Figure 8:
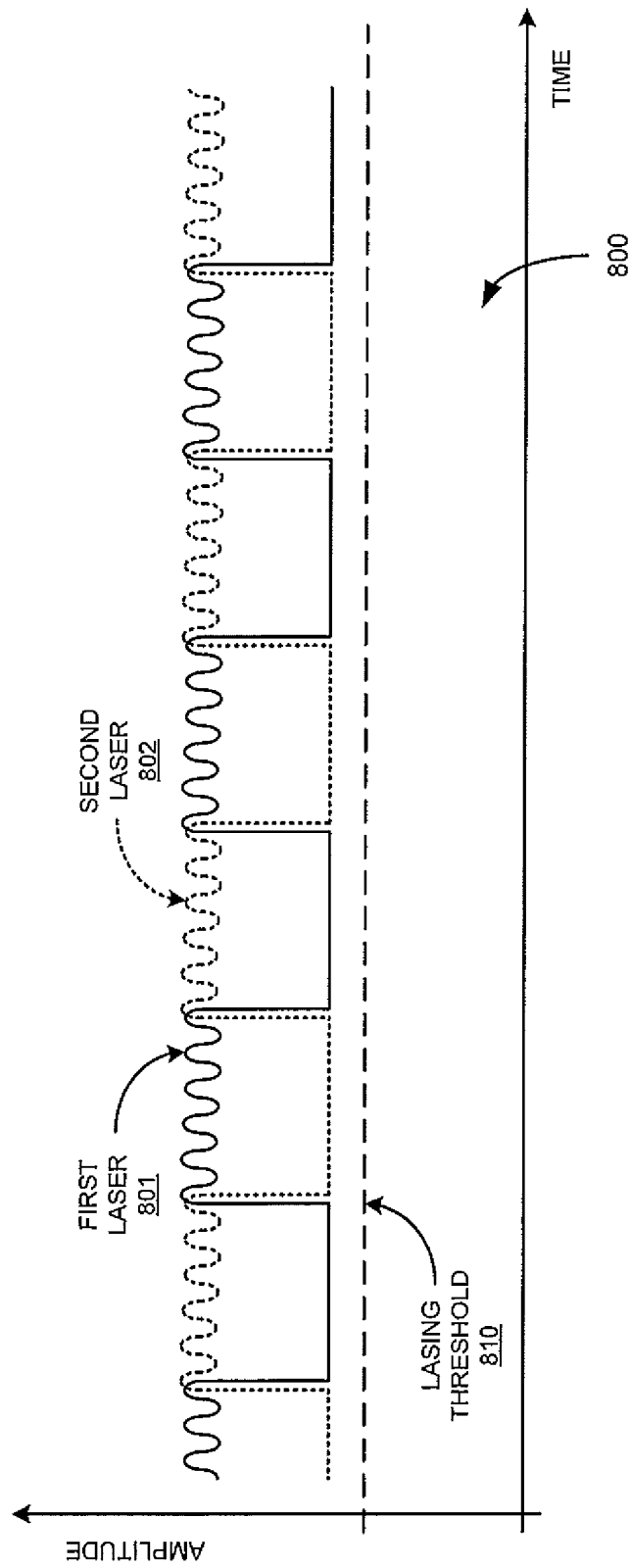
FIG. 8 includes a graph illustrating example laser modulations.

FIG. 8 includes graph 800 illustrating example laser modulations. Graph 800 includes a horizontal time axis and a vertical amplitude axis. The vertical amplitude axis could represent laser power, intensity, or other properties of laser light. Graph 800 includes two representative waveforms, namely first laser 801 and second laser 802. First laser 801 could be a waveform output of laser 324 over optical fiber 371 in FIG. 3, although other configurations could be employed. Second laser 802 could be a waveform output of laser 325 over optical fiber 372 in FIG. 3, although other configurations could be employed. Also, the waveforms in graph 800 are magnified to show details of the modulation waveforms. The modulation waveforms in this example are sinusoidal modulations in the laser light emitted by a laser. It should be understood that different modulation waveforms could be used, and that the number of modulations for each active and inactive period are merely representative of an example duty cycle. It should be understood that the measurement process may employ a different number or duration of active/inactive states as shown in FIG. 8.

The configuration of first laser 801 and second laser 802 in graph 800 indicate a TDM scheme, as discussed herein, where first laser 801 is active when second laser 802 is inactive, and vice versa. Additionally, when in the inactive states, each of first laser 801 and second laser 802 remains emitting laser light above lasing threshold 810. However, when in the inactive state, the modulation signal is not applied to the inactive laser. Therefore, the inactive laser does not turn completely off or go dark, and instead merely dims in intensity to a level just above the lasing threshold and the modulation signal is unapplied. When one of first laser 801 and second laser 802 is directed to become active, the modulation signal is applied in addition to any applicable DC amplitude changes.

In further examples, the modulation amplitudes are larger than that shown in graph 800. The modulation amplitude could vary between a first amplitude and a second amplitude, where the first amplitude is greater than the second amplitude. The second amplitude, namely the minimum value of the modulation, could be tuned to be just above lasing threshold 810, or at lasing threshold 810. In examples where the second amplitude is tuned to be just above lasing threshold 810, when the modulation signal is applied to an unmodulated, or inactive, laser signal, which is still emitting laser light but just above the lasing threshold, then the modulation itself will increase the intensity of the laser according to the modulation frequency. In examples where the second amplitude is tuned to be just below or at lasing threshold 810, when the modulation signal is applied to an unmodulated, or inactive, laser signal, which is off or not emitting laser light, then the modulation itself will turn on the laser or induce the laser to emit light.

FIG. 9 includes graph 900 illustrating example laser modulations. Graph 900 includes a horizontal time axis and a vertical amplitude axis. The vertical amplitude axis could represent laser power, intensity, or other properties of laser light. Graph 900 includes two representative waveforms, namely first laser 901 and second laser 902. First laser 901 could be a waveform output of laser 324 over optical fiber 371 in FIG. 3, although other configurations could be employed. Second laser 902 could be a waveform output of laser 325 over optical fiber 372 in FIG. 3, although other configurations could be employed. Also, the waveforms in graph 900 are magnified to show details of the modulation waveforms. The modulation waveforms in this example are sinusoidal modulations in the laser light emitted by a laser. It should be understood that different modulation waveforms could be used, and that the number of modulations for each active and inactive period are merely representative of an example duty cycle. It should be understood that the blood parameter measurement process may employ a different number of active/inactive states or durations as shown in FIG. 9.

The configuration of first laser 901 and second laser 902 in graph 900 indicate a FDM scheme, as discussed herein. First laser 901 is active when second laser 902 is also active, but are each modulated at different modulation frequencies. When in the inactive state, the modulation signal is not applied to the inactive lasers. When first laser 901 and second laser 902 are directed to become active, the modulation signal is also applied.

Referring back to FIG. 1, processing module 110 comprises communication interfaces, computer systems, microprocessors, circuitry, non-transient computer-readable media, or other processing devices or software systems, and may be distributed among multiple processing devices. Processing module 110 could be included in the equipment or systems of transmission module 120 or receiver module 130, or could be included in separate equipment or systems. Examples of processing module 110 may also include software such as an operating system, logs, utilities, drivers, databases, data structures, processing algorithms, networking software, and other software stored on a non-transient computer-readable medium.

Transmission module 120 comprises electrical to optical conversion circuitry and equipment, optical modulation equipment, and optical waveguide interface equipment. Transmission module 120 could include DDS components, CD/DVD laser driver components, function generators, oscillators, or other signal generation components, filters, delay elements, signal conditioning components, such as passive signal conditioning devices, attenuators, filters, and directional couplers, active signal conditioning devices, amplifiers, or frequency converters, including combinations thereof. Transmission module 120 could also include switching, multiplexing, or buffering circuitry, such as solid-state switches, RF switches, diodes, or other solid state devices. Transmission module 120 also includes laser elements such as a laser diode, solid-state laser, or other laser device, along with associated driving circuitry. Optical couplers, cabling, or attachments could be included to optically mate laser elements to link 160.

Receiver module 130 comprises light detection equipment, optical to electrical conversion circuitry, photon density wave characteristic detection equipment, and analog-to-digital conversion equipment. Receiver module 130 could include a photodiode, phototransistor, avalanche photodiode (APD), or other optoelectronic sensor, along with associated receiver circuitry such as amplifiers or filters. Optical couplers, cabling, or attachments could be included to optically mate receiver module 130 to link 161. Receiver module 130 could also include phase and amplitude detection circuitry and processing elements.

Tissue 140 is a portion of the tissue of a patent undergoing measurement of a physiological blood parameter. It should be understood that tissue 140 could represent a finger, fingertip, toe, earlobe, forehead, or other tissue portion of a patient undergoing physiological parameter measurement. Tissue 140 could comprise muscle, fat, blood, vessels, or other tissue components. The blood portion of tissue 140 could include tissue diffuse blood and arterial or venous blood. In some examples, tissue 140 is a test sample or representative material for calibration or testing of system 100.

Optical links 160-161 each comprise an optical waveguide, and use glass, polymer, air, space, or some other material as the transport media for transmission of light, and could each include multimode fiber (MMF) or single mode fiber (SMF) materials. A sheath or loom could be employed to bundle each of optical links 160-161 together for convenience. One end of each of optical links 160-161 mates with an associated component of system 100, and the other end of each of optical links 160-161 is configured to emit light into tissue 140 or receive light from tissue 140.

Links 170-171 each use metal, glass, optical, air, space, or some other material as the transport media, and comprise analog, digital, RF, optical, or power signals, including combinations thereof. Links 170-171 could each use various communication protocols or formats, such as Controller Area Network (CAN) bus, Inter-Integrated Circuit (I2C), 1-Wire, Radio Frequency Identification (RFID), optical, circuit-switched, Internet Protocol (IP), Ethernet, wireless, Bluetooth, communication signaling, or some other communication format, including combinations, improvements, or variations thereof. Links 170-171 could each be direct links or may include intermediate networks, systems, or devices, and could each include a logical network link transported over multiple physical links.

Communication links 160-161 and 170-171 may each include many different signals sharing the same associated link, as represented by the associated lines in FIG. 1, comprising channels, forward links, reverse links, user communications, overhead communications, frequencies, wavelengths, carriers, timeslots, spreading codes, logical transportation links, packets, or communication directions.

The included descriptions and drawings depict specific embodiments to teach those skilled in the art how to make and use the best mode. For the purpose of teaching inventive principles, some conventional aspects have been simplified or omitted. Those skilled in the art will appreciate variations from these embodiments that fall within the scope of the invention. Those skilled in the art will also appreciate that the features described above can be combined in various ways to form multiple embodiments. As a result, the invention is not limited to the specific embodiments described above, but only by the claims and their equivalents.

What is claimed is:

1. A system for measuring a physiological parameter of blood in a patient, the system comprising:
    a transmission module configured to emit a plurality of photon density waves into tissue of the patient from a plurality of modulated light sources;
    a receiver module configured to detect characteristics of the plurality of photon density waves; and
    a processing module configured to:
        identify time based characteristics of a pulsatile perturbation of the tissue based on the characteristics of the plurality of photon density waves; and
        identify a value of the physiological parameter based on at least the characteristics of the pulsatile perturbation of the tissue and the characteristics of the plurality of photon density waves.

2. The system of claim 1, wherein the physiological parameter comprises a total hemoglobin parameter of the blood of the patient.

3. The system of claim 1, wherein the pulsatile perturbation of the tissue comprises changes in arterial blood volume due to ejection of the blood from the heart of the patient.

4. The system of claim 1, wherein the characteristics of the plurality of photon density waves comprise an amplitude of each of the plurality of photon density waves and a phase delay of each of the plurality of photon density waves.

5. The system of claim 1, wherein the receiver module is configured to detect the plurality of photon density waves scattered through the tissue during the pulsatile perturbation to detect the characteristics of the plurality of photon density waves.

6. The system of claim 1, wherein the plurality of modulated light sources each comprise a modulated laser light of a different wavelength from each other, wherein the transmission module is configured to emit individual wavelengths over ones of a first plurality of optical fibers to emit the plurality of photon density waves into the tissue, and wherein the receiver module is configured to detect the plurality of photon density waves over a second plurality of optical fibers.

7. The system of claim 1, wherein the transmission module comprises:
a switching module configured to sequentially provide a modulation signal to a plurality of light sources to produce the plurality of modulated light sources, wherein each of the plurality of light sources comprises a different wavelength of light.

8. The system of claim 1, wherein the transmission module comprises:
a switching module configured to simultaneously provide a modulation signal to a plurality of light sources to produce the plurality of modulated light sources, wherein each of the plurality of light sources comprises a different wavelength of light.

9. The system of claim 1, further comprising:
a digital direct synthesis module configured to synthesize a modulation drive signal for the plurality of modulated optical signals, wherein the direct digital synthesis module receives instructions on synthesizing the modulation drive signal from the processing module.

10. The system of claim 9, comprising:
the digital direct synthesis module configured to synthesize a modulation reference signal at a predetermined phase delay from the modulation drive signal and provide the modulation reference signal to the processing module;
the processing module configured to identify the characteristics of the plurality of photon density waves based on the modulation reference signal and on at least a scattering of the plurality of photon density waves through the tissue during the pulsatile perturbation.

11. The system of claim 1, further comprising:
a user interface configured to receive the value of the physiological parameter and display the value of the physiological parameter.

12. A system for measuring a physiological parameter of blood in a patient, the system comprising:
a transmission module configured to emit a first modulated optical signal and a second modulated optical signal into tissue of the patient;
a receiver module configured to detect the first modulated optical signal and the second modulated optical signal propagated in the tissue during a pulsatile perturbation;
a processing module configured to:
process the detected first modulated optical signal and the detected second modulated optical signal to determine at least an amplitude and a phase delay of both the detected first modulated optical signal and the detected second modulated optical signal;
determine time based characteristics of the pulsatile perturbation of the tissue based on at least the amplitude and the phase delay of both the detected first modulated optical signal and the detected second modulated optical signal; and
determine a value of the physiological parameter based on at least the characteristics of the pulsatile perturbation of the tissue and the amplitude and the phase delay of both the detected first modulated optical signal and the detected second modulated optical signal.

13. The system of claim 12, wherein the physiological parameter comprises at least one of a total hemoglobin concentration (tHb) parameter, regional oxygen saturation (rSO2) parameter, and arterial oxygen saturation (SpO2) parameter of the blood of the patient.

14. The system of claim 12, wherein the first modulated optical signal comprises a first modulated laser light with a wavelength of 660 nanometers, wherein the second modulated optical signal comprises a second modulated laser light with a wavelength of 808 nanometers, and wherein the modulation frequency of the first modulated optical signal and of the second modulated optical signal is at least 400 megahertz (MHz).

15. The system of claim 14, wherein the first modulated optical signal modulates between a first amplitude and a second amplitude, wherein the first amplitude is greater than the second amplitude, and wherein the second amplitude is at a lasing threshold of the first modulated laser light; and
wherein the second modulated optical signal modulates between a third amplitude and a fourth amplitude, wherein the third amplitude is greater than the fourth amplitude, and wherein the fourth amplitude is at a lasing threshold of the second modulated laser light.

16. The system of claim 12, wherein the transmission module is configured to increase a modulation frequency of at least the first modulated optical signal until the detected phase delay of the detected first modulated optical signal crosses a phase delay threshold.

17. A method of operating a system for measuring a physiological parameter of blood in a patient, the method comprising:
emitting a plurality of photon density waves into tissue of the patient from a plurality of modulated light sources;
detecting characteristics of the plurality of photon density waves;
identifying time based characteristics of a pulsatile perturbation of the tissue based on the characteristics of the plurality of photon density waves; and
identifying a value of the physiological parameter based on at least the characteristics of the pulsatile perturbation of the tissue and the characteristics of the plurality of photon density waves.

18. The method of claim 17, wherein the physiological parameter comprises a total hemoglobin parameter of the blood of the patient.

19. The method of claim 17, wherein the characteristics of the plurality of photon density waves comprise an amplitude of each of the plurality of photon density waves and a phase delay of each of the plurality of photon density waves.

20. The method of claim 17, wherein detecting the characteristics of the plurality of photon density waves comprises detecting the plurality of photon density waves scattered through the tissue during the pulsatile perturbation.

* * * * *